United States Patent
Fleck et al.

(10) Patent No.: US 9,754,415 B2
(45) Date of Patent: Sep. 5, 2017

(54) DISPLAY RELATIVE MOTION COMPENSATION

(71) Applicant: Microsoft Technology Licensing, LLC, Redmond, WA (US)

(72) Inventors: Rod G. Fleck, Bellevue, WA (US); Marshall T. DePue, Redmond, WA (US); David D. Bohn, Fort Collins, CO (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 254 days.

(21) Appl. No.: 14/228,147

(22) Filed: Mar. 27, 2014

(65) Prior Publication Data
US 2015/0279102 A1     Oct. 1, 2015

(51) Int. Cl.
*G06T 19/00* (2011.01)
*A61B 5/11* (2006.01)
(Continued)

(52) U.S. Cl.
CPC .......... *G06T 19/006* (2013.01); *A61B 5/1121* (2013.01); *A61B 5/7445* (2013.01);
(Continued)

(58) Field of Classification Search
None
See application file for complete search history.

(56) References Cited

U.S. PATENT DOCUMENTS

| 5,742,264 A | 4/1998 | Inagaki et al. |
| 6,834,250 B2 | 12/2004 | Uchiyama et al. |

(Continued)

FOREIGN PATENT DOCUMENTS

| EP | 2660645 A1 | 11/2013 |
| JP | H07154829 A | 6/1995 |

(Continued)

OTHER PUBLICATIONS

ISA European Patent Office, International Search Report and Written Opinion Issued in Application No. PCT/US2015/021625, Aug. 4, 2015, WIPO, 12 pages.
(Continued)

*Primary Examiner* — Zhengxi Liu
(74) *Attorney, Agent, or Firm* — Alleman Hall Creasman & Tuttle LLP

(57) ABSTRACT

Embodiments that relate to displaying an image via a display device worn on a head of a user are disclosed. In one example embodiment, an image is displayed at an initial registration position with respect to a user's eye. Composite motion data is received from one or more sensors, with the composite motion data comprising a head motion component and a relative motion component which is relative motion between the head and the display device. The composite motion data is filtered to remove the head motion component and yield the relative motion component. Using the relative motion component, the initial registration position of the image is adjusted to an adjusted registration position that compensates for the relative motion component. The image is then displayed at the adjusted registration position.

18 Claims, 9 Drawing Sheets

(51) Int. Cl.

| | | |
|---|---|---|
| A61B 5/00 | (2006.01) | |
| G02B 27/01 | (2006.01) | |
| G06F 3/01 | (2006.01) | |
| G06K 9/00 | (2006.01) | |
| H04N 13/00 | (2006.01) | |
| H04N 13/04 | (2006.01) | |
| G09G 3/36 | (2006.01) | |
| G06T 7/579 | (2017.01) | |
| G06T 7/246 | (2017.01) | |

(52) U.S. Cl.
CPC ..... *G02B 27/0172* (2013.01); *G02B 27/0179* (2013.01); *G06F 3/011* (2013.01); *G06F 3/012* (2013.01); *G06K 9/00335* (2013.01); *G06T 7/246* (2017.01); *G06T 7/579* (2017.01); *G09G 3/36* (2013.01); *H04N 13/0014* (2013.01); *H04N 13/0429* (2013.01); *G02B 2027/0154* (2013.01); *G02B 2027/0178* (2013.01); *G02B 2027/0187* (2013.01); *G06T 2207/20221* (2013.01); *G06T 2219/016* (2013.01); *H04N 2013/0085* (2013.01)

(56) References Cited

U.S. PATENT DOCUMENTS

| | | |
|---|---|---|
| 7,474,335 B2 | 1/2009 | Basson et al. |
| 8,336,777 B1 | 12/2012 | Pantuso et al. |
| 8,736,692 B1* | 5/2014 | Wong ..................... G06F 3/013 348/208.4 |
| 2006/0140422 A1 | 6/2006 | Zurek et al. |
| 2012/0062445 A1 | 3/2012 | Haddick et al. |
| 2013/0076599 A1 | 3/2013 | Saito |
| 2013/0235169 A1* | 9/2013 | Kato ..................... G02B 27/01 348/53 |

FOREIGN PATENT DOCUMENTS

| | | |
|---|---|---|
| JP | 2002014300 A | 1/2002 |
| JP | 2010232718 A | 10/2010 |
| WO | 2012172719 A1 | 12/2012 |

OTHER PUBLICATIONS

Owen et al., "Display-relative calibration for optical seethrough head-mounted displays", Proceedings of the Third IEEE and ACM International Symposium on Mixed and Augmented Reality (ISMAR 2004); published Nov. 2004; 9 pages.

Rolland et al., "A method of Computational Correction for Optical Distortion in Head-Mounted Displays", published 1993; 14 pages.

Luo et al., "Registration of an on-axis see-through head-mounted display and camera system", Optical Engineering, vol. 44(2); published Feb. 2005, 7 pages.

IPEA European Patent Office, International Preliminary Report on Patentability Issued in Application No. PCT/US2015/021625, Jun. 3, 2016, WIPO, 10 Pages.

IPEA European Patent Office, Second Written Opinion Issued in Application No. PCT/US2015/021625, Mar. 2, 2016, WIPO, 7 pages.

* cited by examiner

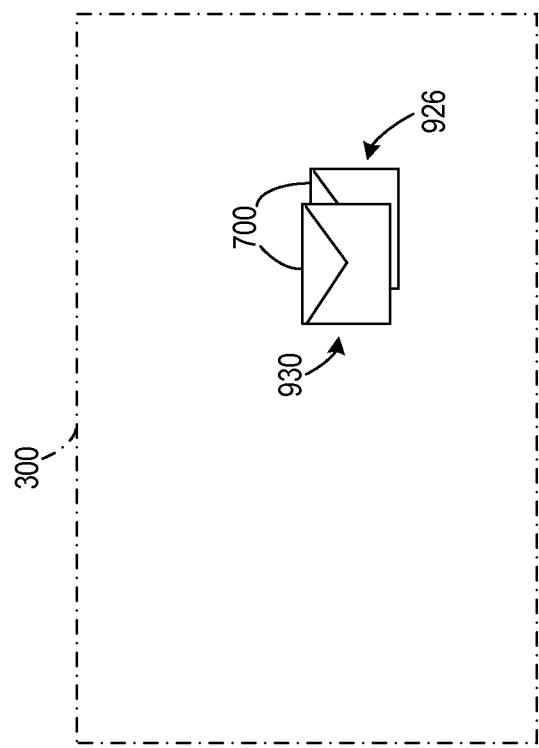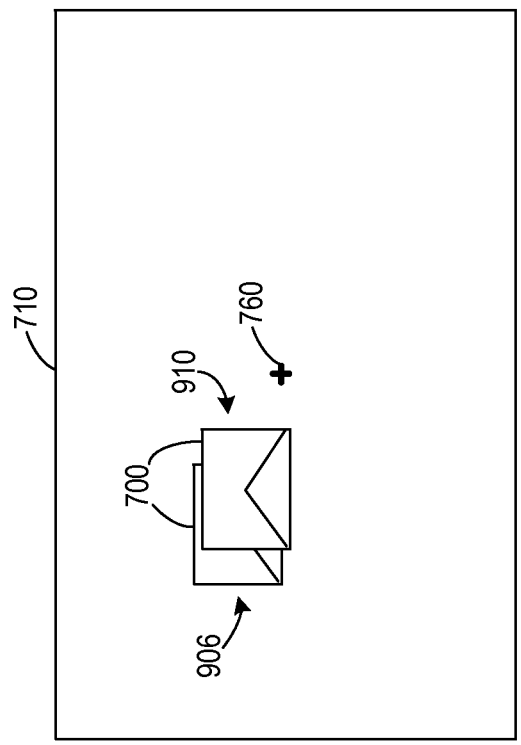
FIG. 9

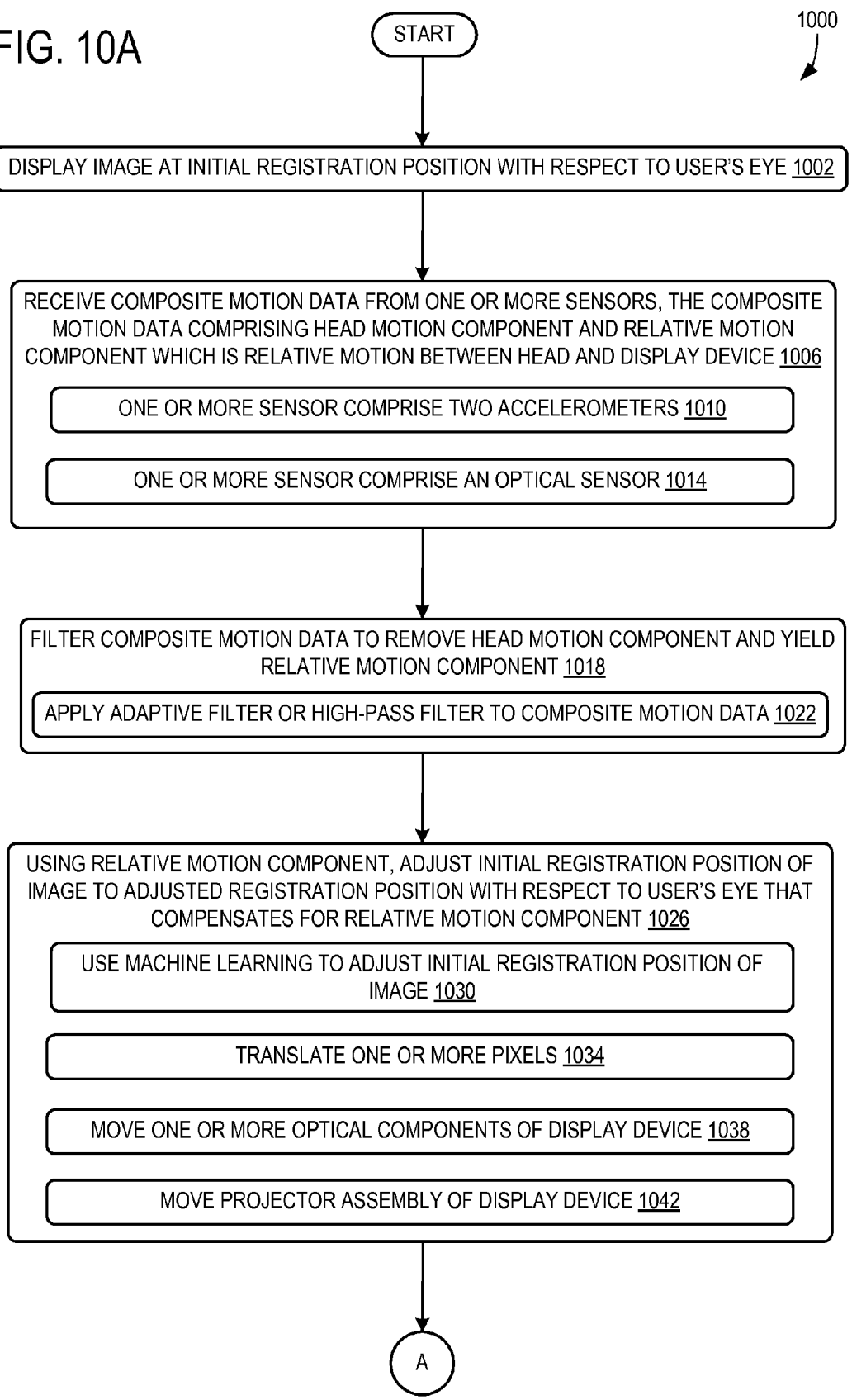

DISPLAY RELATIVE MOTION COMPENSATION

BACKGROUND

Head-mounted display (HMD) devices may generate images viewed by the eyes of a user. The location of a displayed image will shift when the HMD device and/or display components of the device move relative to the user's head. For example, when a user wearing an HMD device walks or runs, vibrations and other movements of the user's head may cause the HMD device to move relative to the user's head and eyes. Such relative movement can disrupt the display of images through image blurring, image jitter, and other motion-induced artifacts, thereby compromising viewing comfort. Among other issues, this can impair the user's ability to discern small objects, read small text, and can otherwise degrade the viewing experience.

To reduce such unwanted relative movement, some HMD devices utilize a tightly fitted helmet, headset, full-head wrapped solution, or other constrained coupling of the device to the user's head. However, lighter weight and smaller form factor HMD devices, such as devices utilizing eyeglass or similar frames, are ill-suited for such bulky and tight coupling solutions. Further, because eyeglasses and other wearable display devices are typically worn somewhat loosely for comfort, undesirable movement of such devices relative to the user's head may be more frequently encountered.

SUMMARY

Various embodiments are disclosed herein that relate to displaying an image via a display device worn on a head of a user. For example, one disclosed embodiment provides a method that includes displaying an image at an initial registration position with respect to an eye of the user. Composite motion data is received from one or more sensors of the display device, with the composite motion data comprising a head motion component and a relative motion component which is relative motion between the head and the display device.

The composite motion data is filtered to remove the head motion component and yield the relative motion component. Using the relative motion component, the initial registration position of the image is adjusted to an adjusted registration position with respect to the user's eye that compensates for the relative motion component. The image is then displayed at the adjusted registration position.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 9 is a schematic view of the user's cornea and the corresponding viewing region showing adjustments to the registration position of the displayed image according to another embodiment of the present disclosure.

FIGS. 10A and 10B are a flow chart of a method for displaying an image according to an embodiment of the present disclosure.

DETAILED DESCRIPTION

Figure 1:
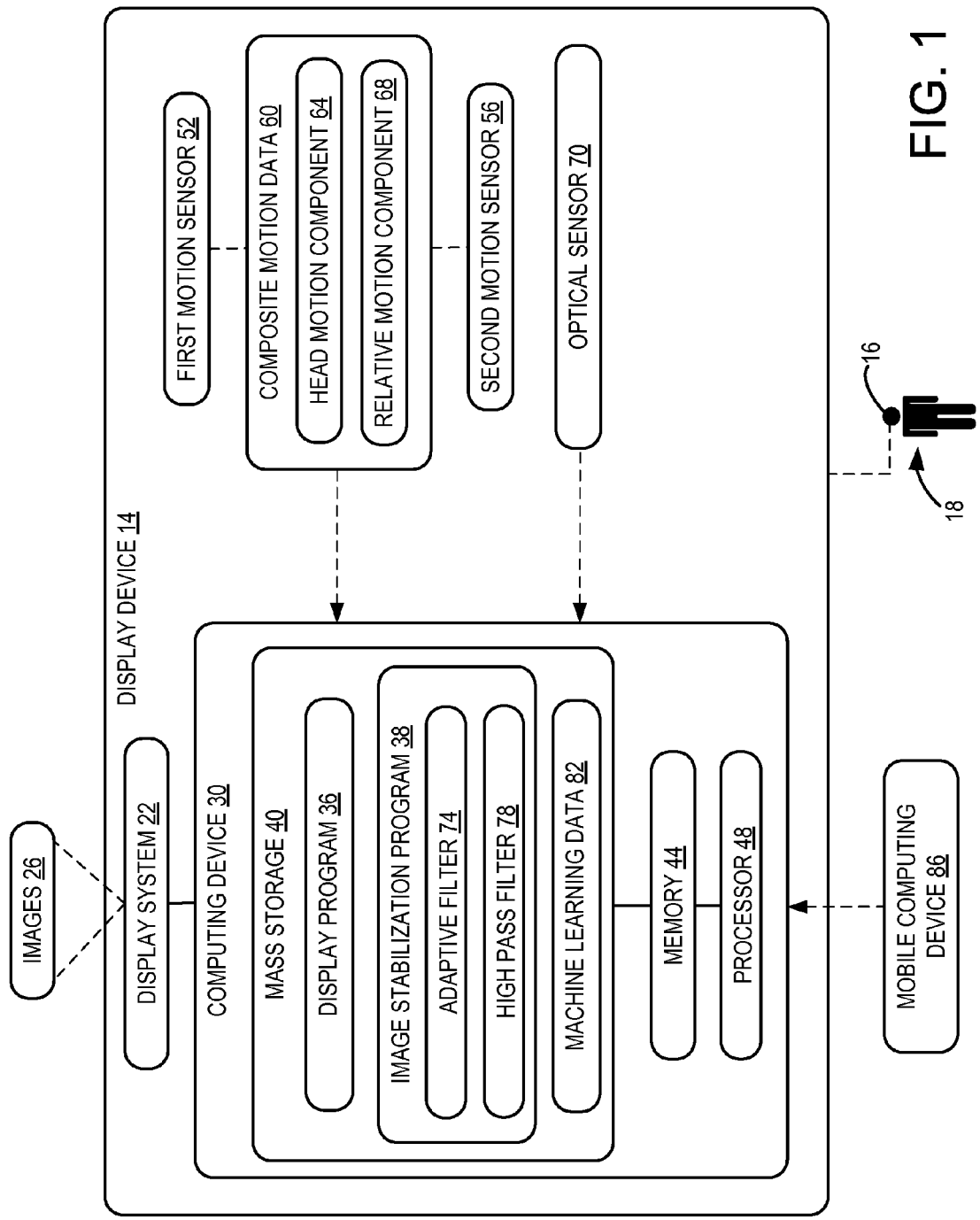
FIG. 1 is a schematic view of a display device configured to be worn on a head according to an embodiment of the present disclosure.

FIG. 1 shows a schematic view of one embodiment of a display device 14 that is configured to be worn on the head 16 of a user 18. In the example shown in FIGS. 2 and 3 and described in more detail below, the display device 14 may take the form of eyeglasses 200. The display device 14 includes a display system 22 that is configured to display images 26 for viewing by the user 18.

The display device 14 is operatively connected to a computing device 30 that includes a display program 36 for controlling the display system 22. Additionally and as described in more detail below, the computing device 30 includes an image stabilization program 38 that interfaces with the display program 36 to adjust a registration position of an image 26 with respect to an eye of the user to compensate for relative motion between the user's head 16 and the display device. The display program 36 and image stabilization program 38 may be stored in mass storage 40 of the computing device 30, loaded into memory 44 and executed by a processor 48 of the computing device 30 to perform one or more of the methods and processes described in more detail below.

The example illustrated in FIG. 1 shows the computing device 30 integrated into the display device 14. It will be appreciated that in other examples the computing device 30 may be a component or device that is separate from the display device 14. In these examples the computing device 30 may take the form of a mobile computing device such as a smart phone, laptop, notebook or tablet computer, desktop computing device, network computer, home entertainment computer, interactive television, gaming system, or other suitable type of computing device.

The computing device 30 may be operatively connected with the display device 14 using a wired connection, or may employ a wireless connection via WiFi, Bluetooth, or any other suitable wireless communication protocol. Additional details regarding the components and computing aspects of the computing device 30 are described in more detail below with reference to FIG. 11.

Figure 2:
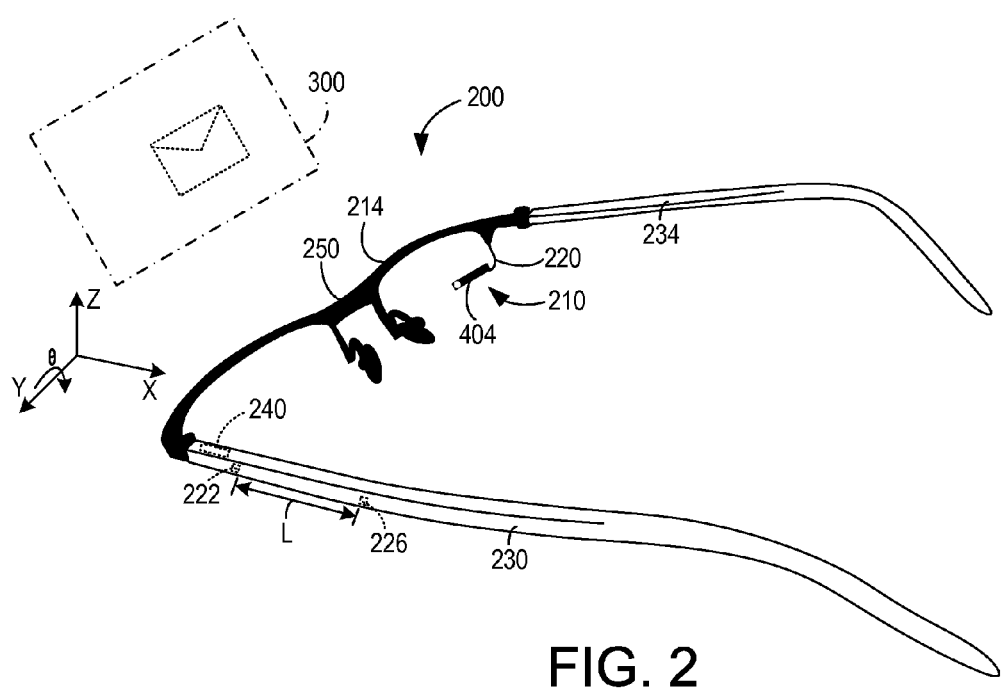
FIG. 2 is a schematic perspective view of an example display device according to an embodiment of the present disclosure.
Figure 3:
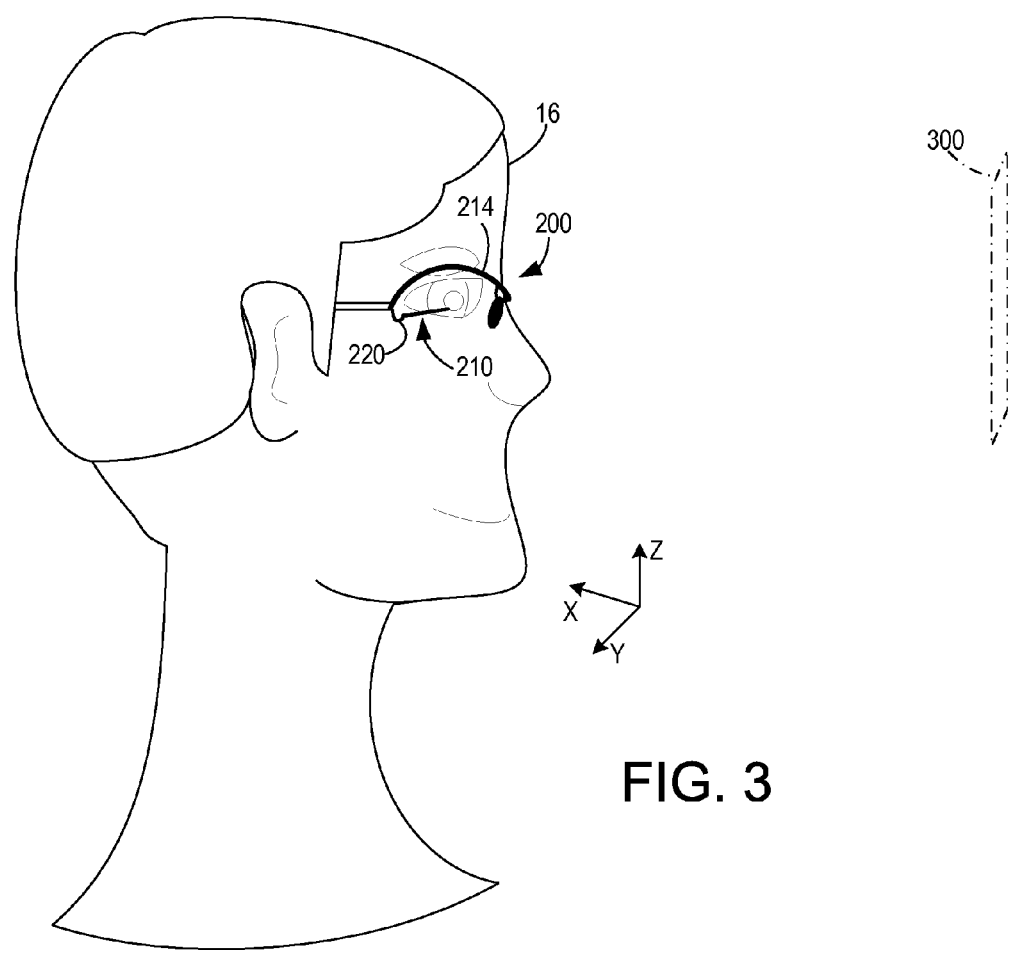
FIG. 3 is a schematic side view of a user wearing the display device of FIG. 2.

With reference now also to the example shown in FIGS. 2 and 3, the display device 14 may comprise a head-mounted display (HMD) device in the form of eyeglasses 200 that generate images creating a virtual reality or mixed reality experience. In this example the eyeglasses 200 include a micro-display 210 that is supported in front of a user's eye via a support arm 220 and display bridge 214. It will be appreciated that in other examples, the eyeglasses 200 may take other suitable forms in which a micro-display or other type of transparent, semi-transparent or non-transparent display is supported in front of a viewer's eye or eyes. It will also be appreciated that many other types and configurations of wearable display devices having various form factors may also be used within the scope of the present disclosure.

With reference to the eyeglasses 200 shown in FIGS. 2 and 3, in this example the micro-display 210 may be configured to project one or more images into the eye of a user. In this manner, the appearance of the user's physical environment may be augmented by graphical content (e.g., one or more images each having a respective color and brightness) that is presented via the micro-display 210. In this example and with reference also to FIGS. 4 and 5, the micro-display 210 includes a projector assembly 400 and a pipe portion 404 extending from a light-emitting side 408 of the projector assembly. A support arm 220 extends from a bottom side 412 of the projector assembly 400 and connects the micro-display 210 to the display bridge 214.

Figure 4:
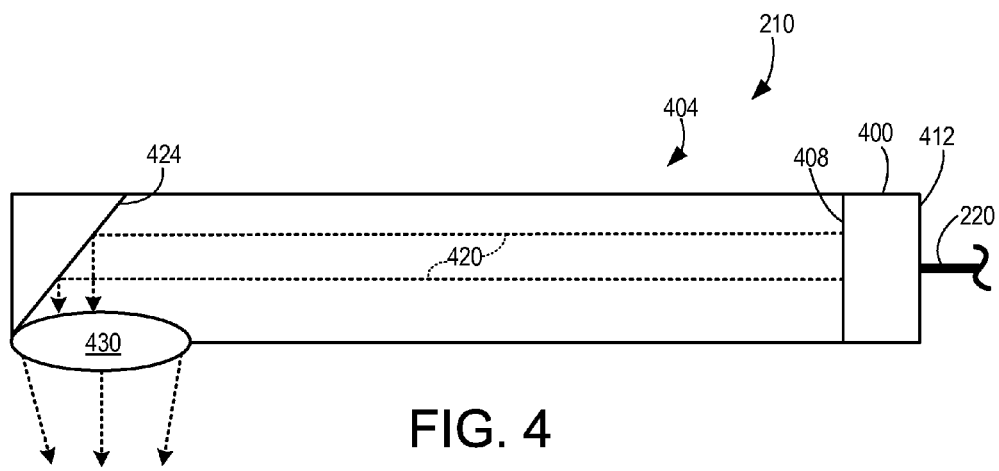
FIG. 4 is a schematic top view of a display system of the display device of FIG. 2 according to an embodiment of the present disclosure.
Figure 5:
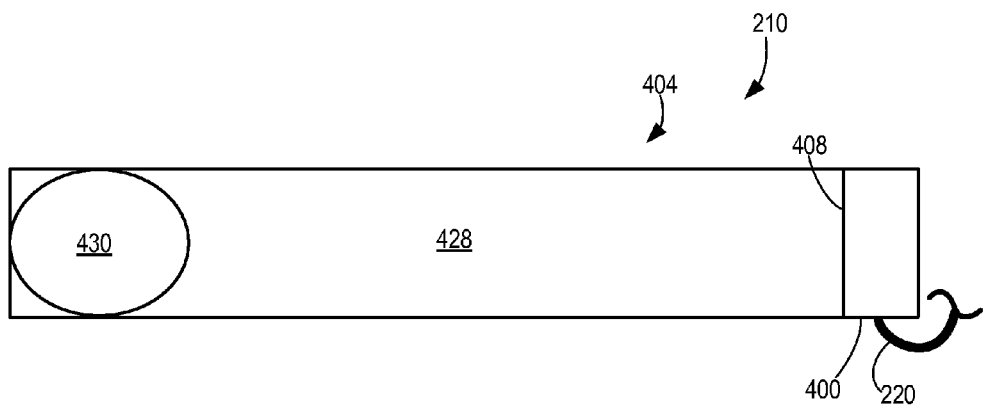
FIG. 5 is a schematic view from the perspective of a user's eyeball of the display system of FIG. 4.

As schematically shown in FIG. 4, light rays 420 projected from the projector assembly 400 may be transmitted down the pipe portion 404 and guided by, for example, one or more mirrors 424. One or more optical elements such as lens 430 collect the reflected light rays and direct the rays outwardly from the pipe portion 404 into the user's eye. In this manner, images may be displayed to the user 18. In this example an outer surface 428 of the pipe portion 404 of the micro-display 210 is opaque such that the user 18 cannot see through the outer surface. In some examples, the micro-display 210 may provide a Wide VGA (WVGA) display resolution such as for example, 720×480 pixels, 800×480 pixels, or 854×480 pixels (Full Wide VGA resolution). It will also be appreciated that in other examples the micro-display 210 may provide other display resolutions.

In some examples the lens 430 may set the location of the virtual image between approximately 0.5 meters (m) and 3.5 m, or between approximately 1.0 m and 3.0 m, or at approximately 2.0 m from the lens, or at the near point of the human eye (arm's length), or even at infinity. In this manner, images 26 displayed by the micro-display 210 may be perceived by the user 18 to float in front of the user. With reference again to FIGS. 2 and 3 and as described in more detail below, in some examples images 26 may be perceived by the user 18 to be displayed in a viewing region 300 that may be located at any point between the near point of the eye, approximately one foot from the eye, all the way to infinity.

Continuing with FIGS. 2 and 3, the small form factor of the micro-display 210 enables the user 18 to view the physical environment with the eye facing the micro-display by easily looking over, under and around the micro-display. For example, in one example embodiment the micro-display 210 may have a length of approximately 10 mm and a square cross-section having sides of approximately 6 mm each. Other dimensions and cross-sectional profiles may also be utilized. It will also be appreciated that by utilizing one micro-display 210 for the user's right eye, the eyeglasses 200 also allow the user 18 to freely view the physical environment with the user's left eye.

Figure 6:
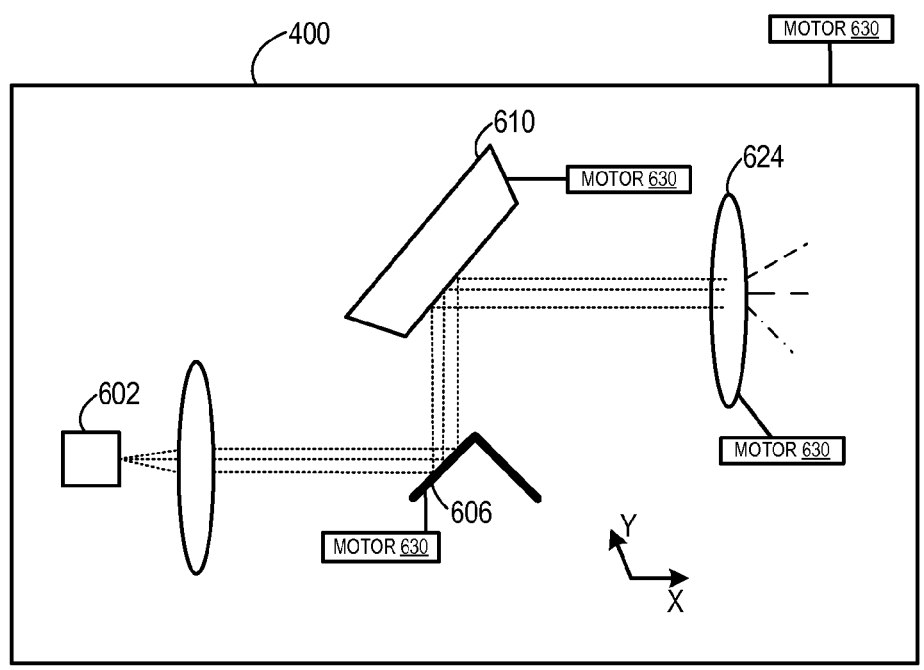
FIG. 6 is a schematic exploded view of an example display system of the display device of FIG. 2.

In one example and with reference now to FIG. 6, the projector assembly 400 of the micro-display 210 may comprise liquid crystal on silicon (LCOS) display technology and various optical components. In this example the projector assembly 400 includes a light source 602 and a mirror 606 that guides the emitted light to a single reflective LCOS panel 610. The light source 602 may sequentially illuminate the LCOS panel 610 with red, green and blue light. The LCOS panel 610 may then reflect the light to exit optics 624 which introduce the light into the pipe portion 404. In other examples the projector assembly 400 may utilize a single LCOS panel with RGB filters that receive white light emitted from a light source. In other examples, the projector assembly 400 may utilize a single RBGOrganic Light-Emitting Diode (OLED) panel.

One or more of the optical components of the projector assembly 400 may be moveable by one or more motors or actuators. In one example the mirror 606 may be coupled to a piezo electric motor 630 that may be actuated to adjust a position or orientation of the mirror. In another example, the LCOS panel 610 may be coupled to a piezo electric motor 630 that may be actuated to laterally shift the panel. In other examples, the entire projector assembly 400 may be coupled to a piezo electric motor 630 that may be actuated to adjust a position or orientation of the assembly. In other examples, the exit optics 624 of the micro-display 210 may similarly be coupled to a motor 630 that may adjust a position or orientation of the exit optics. In the foregoing examples, the projector assembly 400 may be sized appropriately to accommodate the movement of components, and a position and size of an eyebox may be correspondingly adjusted.

In this manner and as described in more detail below, a registration position of an image 26 may be adjusted to compensate for relative motion between the eyeglasses 200 and the head 16 of the user 18. It will be appreciated that motors other than piezo electric motors may also be utilized such as, for example, ultrasonic motors, voice coils, etc. It will also be appreciated that any suitable combination and configuration of motors coupled to one or more optical elements may be utilized to adjust the registration position of an image 26.

In other examples, the micro-display 210 may utilize other configurations and/or display technologies including, but not limited to, transmissive LCOS displays, light modulators and transparent light guides, Light-Emitting Diode (LED) arrays, Organic Light-Emitting Diode (OLED) displays, and asymmetric projection and associated optics.

The eyeglasses 200 may further include one or more sensors that detect movement of the eyeglasses, such as acceleration, position tracking, and/or orientation sensing of the eyeglasses. With reference again to FIGS. 1 and 2, in one example the eyeglasses may include a first motion sensor 52 and a second motion sensor 56. The first motion sensor 52 and second motion sensor 56 may each comprise, for example, a two-axis or two degree-of-freedom accelerometer to indicate or measure a change in location of the eyeglasses 200 within two-dimensional space along two orthogonal axes (e.g., x and y). For example, each accelerometer may measure translation along the two axes.

With reference now to FIG. 2, in one example the first motion sensor 52 may comprise a first two-axis accelerometer 222 and the second motion sensor 56 may comprise a second two-axis accelerometer 226. The first two-axis accelerometer 222 and the second two-axis accelerometer 226 may be integrated into the left temple arm 230 of the eyeglasses 200. Using a differential measurement of the signals generated by the first accelerometer 222 and the second accelerometer 226, motion of the eyeglasses 200 and/or head 16 may be determined. For example, a pitch θ of the eyeglasses 200 about the Y-axis may be determined by making a differential measurement using a formula:

$$d\theta = \text{Constant} * (VA1 - VA2) * L;$$

where the value of Constant depends upon the manufacturer and operating conditions of the particular accelerometer being used; VA1=voltage signal from the first accelerometer 222; VA2=voltage signal from the second accelerometer 226; and L=a linear distance between the two accelerometers. As an example, the Analog Devices ADXL322, is a small and thin accelerometer used in mobile phones, with a full scale range of +/−2 g, an output sensitivity that is typically 750 mV/g (at a 5V supply rail), where g=acceleration due to gravity=9.8 m/s^2. When the ADXL322 is oriented perpendicular to gravity, its output changes by 17.5 mg per degree.

Angular sensitivity of this two accelerometer configuration may be adjusted by changing the distance L between the accelerometers. As described in more detail below, the dθ value may be used as an error signal to adjust the registration position of an image 26 with respect to the eyeglasses 200 prior to displaying the image to the user 18.

It will be appreciated that the above example configuration of accelerometers is provided for descriptive purposes, and that other configurations of one or more motions sensors may also be utilized to detect movement of the eyeglasses 200. For example, a pair of accelerometers may be integrated into the right temple arm 234 of the eyeglasses 200. In other examples, one or more three-axis accelerometers may be utilized to measure a change in location of the eyeglasses 200 within three-dimensional space along three orthogonal axes (e.g., x, y and z). In other examples, one or more gyroscopes may be utilized to determine three-axis acceleration around the x, y and z axes.

As described in more detail below and with reference to FIG. 1, composite motion data 60 may be received from the first motion sensor 52 and second motion sensor 56. Such composite motion data 60 may comprise a head motion component 64 that represents relatively low frequency motion corresponding to head movement, and a relative motion component 68 that represents relatively high frequency motion that may be caused by quick movements, shaking or jitter of the eyeglasses 200. As described in more detail below, such high frequency motion may correspond to undesirable relative movement between the eyeglasses 200 and the head 16 of the user 18, which can blur and otherwise degrade displayed images 26. Advantageously and as described in more detail below, the image stabilization program 38 may filter the composite motion data 60 to remove the head motion component 64 and yield the relative motion component 68. The relative motion component may then be used to adjust a registration position of an image 26 to compensate for the relative motion between the eyeglasses 200 and head 16 of the user 18.

In other examples the eyeglasses 200 may also include other suitable positioning components, such as a compass, global positioning system (GPS) or other navigation systems. The eyeglasses 200 may also include one or more microphones to determine sound direction data, which may be used to enhance the determination of relative motion of the eyeglasses.

In some examples the eyeglasses 200 may also include various other sensors and related systems. For example, the eyeglasses 200 may include one or more optical sensor(s) 70 that may capture image data to detect movement of the eyeglasses and/or head 16 of the user 18. In one example and with reference to FIG. 2, the eyeglasses 200 may include an inwardly-facing CMOS detector 240 that images surface detail from the user's head skin and/or hair to determine motion of the left temple arm 230 with respect to the skin and/or hair. Such motion may correspond to relative movement between the eyeglasses 200 and the user's head 16. In some examples the CMOS detector 240 may comprise an LED light source and either a single lens or a microlens array to guide the emitted and reflected light rays. It will also be appreciated that the inwardly-facing CMOS detector may be positioned at any suitable location on the eyeglasses 200. Further, any suitable optical sensor technology and configuration may be utilized for an inwardly-facing optical detector. For example, the laser or LED, lens and CMOS sensor found in an optical mouse may be used as a relative motion detector between eyeglasses and head.

In other examples, the one or more optical sensor(s) 70 may include an outwardly-facing sensor, such as a camera (not shown) facing away from the user's head 16 and located at a nose bridge portion 250 of the display bridge 214. The camera may capture two-dimensional image information and/or depth information from the physical environment and physical objects within the environment of the user 18. For example, the camera may include a depth camera, a visible light camera, an infrared light camera, and/or a position tracking camera.

In one example, the camera may comprise a depth camera that includes left and right cameras of a stereoscopic vision system. Time-resolved images from one or more of these depth cameras may be registered to each other and/or to images from another optical sensor such as a visible spectrum camera, and may be combined to yield depth-resolved video.

In other examples a structured light depth camera may be configured to project a structured infrared illumination, and to image the illumination reflected from a scene onto which the illumination is projected. A depth map of the scene may be constructed based on spacings between adjacent features in the various regions of an imaged scene. In still other examples, a depth camera may take the form of a time-of-flight depth camera configured to project a pulsed infrared illumination onto a scene and detect the illumination reflected from the scene. It will be appreciated that any other suitable depth camera may be used within the scope of the present disclosure.

As noted above, the eyeglasses 200 may include an integrated computing device 30 having a logic subsystem and a storage subsystem, as discussed in more detail below with respect to FIG. 11, that are in communication with the various sensors and systems of the eyeglasses. In other examples where the eyeglasses 200 are communicatively connected to a separate computing device, the storage subsystem may include instructions executable by the logic subsystem to receive signal inputs from the sensors and forward such inputs to the computing device (in unprocessed or processed form), and to present images to a user via the display system 22.

It will be appreciated that the eyeglasses 200 and related sensors and other components described above and illustrated in FIGS. 1-6 are provided by way of example. These examples are not intended to be limiting in any manner, as any other suitable sensors, components, and/or combination of sensors and components may be utilized. Therefore it is to be understood that the eyeglasses 200 may include additional and/or alternative sensors, cameras, microphones, input devices, output devices, etc. without departing from the scope of this disclosure.

Figure 8:
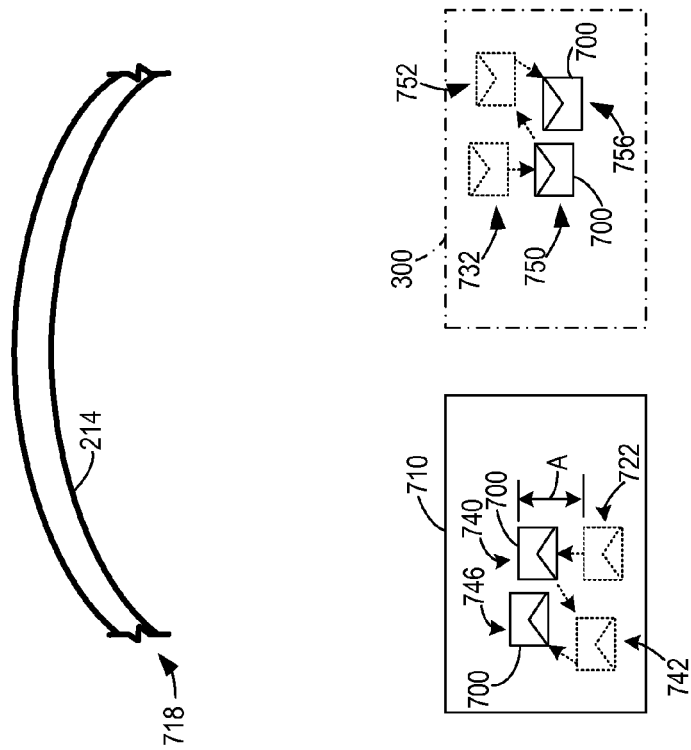
FIG. 8 is a schematic view of the portion of the user's cornea, the corresponding viewing region and the portion of the display device of FIG. 7 showing the portion of the display device in the subsequent position and adjustments to the registration position of the displayed image.

Descriptions of example embodiments and use cases of the display device 14 will now be provided. FIGS. 1 and 8 provide a schematic view of an envelope image 700 projected onto the cornea 710 of the user's eye by the microdisplay 210, and a corresponding schematic view from the perspective of the user's eye of a viewing region 300 in which the image of the envelope is perceived by the user 18. For purposes of the present disclosure and with reference also to FIGS. 2 and 3, the viewing region 300 may be defined as a two-dimensional region in space in which the user 18 perceives an image 26 to be located. Also schematically shown in FIGS. 7 and 8 is a portion of the display bridge 214 of the eyeglasses 200.

Figure 7:
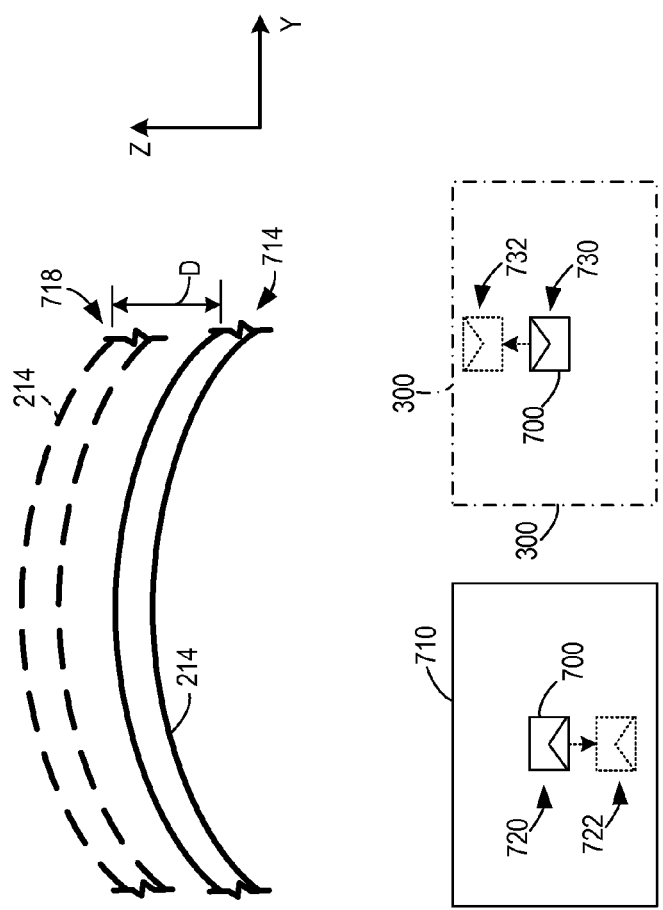
FIG. 7 is a schematic view of a portion of a user's cornea onto which an image is projected, a corresponding viewing region depicting the image as perceived by the user, and a portion of the display device of FIG. 2 in initial and subsequent positions.

As described in more detail below, FIGS. 7 and 8 illustrate relative movement of the eyeglasses 200 with respect to the head 16 of the user 18 by showing movement of the display bridge 214 and a corresponding displacement of the envelope image 700 as projected on the cornea 710 of the user's eye. FIGS. 7 and 8 also show the corresponding displacement of the envelope image 700 as would be perceived by the user 18 within the viewing region 300.

It will be appreciated that with the eyeglasses 200 seated on the user's nose and head 16, many ordinary movements of the head, such as head turning and/or rotation to look in a different direction, or head translation induced by user locomotion, will generally result in the eyeglasses 200 undergoing the same movements. Alternatively expressed, during movement of the user's head 16 in which the eyeglasses 200 remain stationary such that no relative movement between the head and eyeglasses occurs, the envelope image 700 remains stationary at an initial registration position 720 with respect to the eye and cornea 710. Correspondingly, during such movements the envelope image 700 as perceived by the user also remains stationary at an initial perceived position 730 with respect to the viewing region 300.

Further, many of these ordinary movements of the eyeglasses 200 will correspond to relatively slow accelerations of the eyeglasses, which in turn correspond to relatively low frequency output signals from the first accelerometer 222 and second accelerometer 226. As an example of the above-described ordinary movements of the eyeglasses 200, consider the case of running or walking by the user. These activities provide an output signal with frequency content that is indicative of the user's gross motion and vary depending upon the activity level. Fast running (at 240 steps per minute for the fastest 10K runners) yields a frequency spectrum peaked near approximately 4 Hz, while walking (at 20 steps per minute) is a periodic signal with frequency content ~⅓ Hz. In FIG. 1 such movements are represented in the composite motion data 60 by the head motion component 64.

By contrast, relative movement between the head 16 and eyeglasses 200 causes corresponding and undesirable movement of the envelope image 700 on the cornea 710. As noted above, such relative movement results in image blurring, jitter and other image quality issues. Additionally, relative movement between the eyeglasses 200 and the head 16 often corresponds to relatively fast accelerations of the eyeglasses, which in turn correspond to relatively high frequency output signals from the accelerometers. Relative motion between the head and the eyeglasses may also appear at a spread of frequencies, rather than a periodic or quasi-periodic signal. For example, if the eyeglasses quickly slip or move on the head in a time deltaT seconds, the output signal spectrum from the accelerometers will contain frequency content deltaFrequency=1/deltaT. Such motion might result from a gust of wind, for example.

In one example where the user 18 is running on asphalt while wearing the eyeglasses 200, the composite motion data 60 will include a head motion component 64 corresponding to synchronous movement of the eyeglasses 200 and user head 16. The eyeglasses 200 may also experience shaking or vibration caused by the user's footfalls. Such shaking or vibration will often correspond to relatively fast accelerations of the eyeglasses. Additionally, often such shaking or jitter will also correspond to the undesirable relative movement described above. In FIG. 1 such relative motion is represented in the composite motion data 60 by the relative motion component 68.

Advantageously and as described in more detail below, the image stabilization program 38 may filter composite motion data 60 to remove the head motion component 64 and yield the relative motion component 68. The relative motion component 68 may then be used to adjust a registration position of an image 26 to compensate for the relative motion between the eyeglasses 200 and head 16 of the user 18. The image 26 may then be displayed at the adjusted registration position.

In some examples, the image stabilization program 38 may apply an adaptive filter 74 to the composite motion data 60 to remove the head motion component 64 and yield the relative motion component 68. For example, a Kalman filter, least means squared filter, recursive least squares filter, or other suitable adaptive filter that self-adjusts its transfer function according to an optimization algorithm driven by output signals from the accelerometers may be utilized. In other examples, the image stabilization program 38 may apply a non-adaptive, high-pass filter 78 to the composite motion data 60 to remove the head motion component 64 and yield the relative motion component 68.

In some examples and in addition to or instead of a filter, the image stabilization program 38 may utilize one or more machine learning procedures to analyze the composite motion data 60. Such machine learning procedures may, over time, generate machine learning data 82 that is used by the image stabilization program 38 to adjust a registration position of an image 26 to compensate for relative motion between the eyeglasses 200 and head 16. Machine learning procedures may include, but are not limited to, Bayesian structure search, Support Vector Machines, Gaussian Processes, logistic regression, and extensions to relational variants that take into consideration constraints or patterns of relationship among entities or properties.

Returning to FIGS. 7 and 8 and as noted above, these figures illustrate relative movement of the eyeglasses 200 with respect to the head 16 of the user 18 by showing movement of the display bridge 214 and a corresponding displacement of the envelope image 700 as projected on the cornea 710 of the user's eye. In FIG. 7 the portion of the display bridge 214 of the eyeglasses 200 is shown in an initial position 714 and in a subsequent position 718 that is displaced in a vertical direction along the Z-axis with respect to the eye of the user 18.

At the initial position 714 of the display bridge 214, the envelope image 700 is displayed at the initial registration position 720 on the cornea 710. This initial registration position 720 corresponds to the initial perceived position 730 in the viewing region 300. At the subsequent position 718 of the display bridge 214 and because the display system 22 has been displaced in the Z-axis direction, if displayed the envelope image 700 would be located at a displaced registration position 722 on the cornea 710 and at a displaced perceived position 732 in the viewing region 300. If displayed in these positions, the envelope image 700 would be perceived by the user to have jumped to the displaced perceived position, and over additional, repeated relative movements may appear blurry to the user.

With reference now to FIG. 8, after filtering the composite motion data 60 to remove the head motion component 64 and yield the relative motion component 68 as described above, and instead of displaying the envelope image 700 at the displaced registration position 722, the image stabilization program 38 may use the relative motion component 68 to adjust the displayed location of the envelope image 700 to an adjusted registration position 740 that compensates for the relative motion component 68.

In one example, the image stabilization program 38 may utilize the relative motion component 68 to estimate a distance D that the display bridge 214 has been displaced in the Z-axis direction. Using the distance D and the optical configuration of the display system 22, the image stabilization program 38 may determine an adjustment A in the Z-axis direction by which to adjust the displaced registration position 722 to the adjusted registration position 740. In this manner, after the eyeglasses 200 have moved relative to the head 16 of the user 18, the image stabilization program 38 adjusts the display of the envelope image 700 to the adjusted registration position 740 which more closely matches the initial registration position 720 prior to such relative movement. The adjusted registration position 740 also corresponds to an adjusted perceived position 750 as compared to the displaced perceived position 732 in the viewing region 300. Advantageously, with these corrections the user experiences less jitter and blur when viewing the envelope image 700 during such relative movement.

FIG. 8 also illustrates a subsequent relative movement between the eyeglasses 200 and the head 16 of the user 18 in which the eyeglasses move relative to the head in Z-axis and Y-axis directions. According to this subsequent relative movement, if displayed the envelope image 700 would be located at a second displaced registration position 742 on the cornea 710 and at a second displaced perceived position 752 with respect to the viewing region 300. The image stabilization program 38 may similarly adjust the display of the envelope image 700 to a second adjusted registration position 746 which more closely matches the adjusted registration position 740 prior to such relative movement. The second adjusted registration position 746 also corresponds to a second adjusted perceived position 756 in the viewing region 300.

As noted above, in some examples the image stabilization program 38 may adjust the registration position of an image 26 by moving one or more optical components of the display device 14. In other examples, the entire projector assembly 400 of the micro-display 210 may be moved to adjust the registration position of an image 26. In other examples, the image stabilization program 38 may adjust the registration position of an image 26 by translating one or more pixels of the image. For example and with reference again to FIG. 6, individual liquid crystals in the reflective LCOS panels 606, 610 and 614 may be selectively opened and closed to translate corresponding pixels of the generated image. It will be appreciated that with other display technologies, other methods of translating pixels of the image may be utilized.

In some examples, the image stabilization program 38 may adjust the registration position of an image 26 as described above at a stabilization frequency. Examples of stabilization frequencies that may be utilized include, but are not limited to, 30 Hz., 60 Hz., 120 Hz., or any other suitable frequency. A lower frequency, for example between 1 Hz to 30 Hz, may be chosen to optimize the battery life and computation vs. user perception trade-off. It will also be appreciated that in some examples, as the registration position of an image 26 is continually adjusted over time, the location of the image may approach an edge or boundary of the display system's available imaging area. Accordingly and with reference now to FIG. 9, in some examples the image stabilization program 38 may, at a centering frequency that is slower than the stabilization frequency, progressively display the image 26 at locations increasingly closer to a reference location 760 on the cornea 710.

In some examples the centering frequency may be 5, 10, 20, or other multiple times slower than the stabilization frequency. The reference position may be, for example, an approximate location of the fovea of the user's eye, or any other suitable reference position that provides sufficient surrounding display area.

As shown in the example of FIG. 9, the envelope image 700 may be displayed at a registration position 906 on the cornea 710, which corresponds to a perceived position 926 in the viewing region 300. The image stabilization program 38 may then adjust the location of the envelope image 700 to an adjusted registration position 910 that is closer to the reference location 760. The adjusted registration position 910 corresponds to an adjusted perceived position 930 in the viewing region 300. As noted above, such adjustments may be performed at a centering frequency that is slower than the stabilization frequency. Additionally, the magnitude of such centering adjustments may be relatively small to minimize any visual perception of such adjustments by the user 18. In some examples, each such centering adjustment may comprise a one pixel translation of the image.

In other examples and with reference again to FIG. 1, a companion device such as a mobile computing device 86 may provide companion sensor data to the display device 14 that also may be used to adjust the registration location of an image 26 to compensate for relative motion. In this manner, the accuracy of such adjustments may be improved. For example, where the mobile computing device 86 is a smart phone that includes one or more accelerometers, composite motion data from the smart phone also may be provided to the display device. The display device 14 may also determine the proximity of the smart phone to the display device.

If the proximity is less than a predetermined threshold, such as 1 m. for example, the display device 14 may determine that composite motion data from the smart phone corresponds to motion events experienced by the user 18 wearing the display device 14. One example of this situation is where the user 18 is riding in a car and has the smart phone in the user's pocket. In this case, the display device 14 determines that composite motion data from the smart phone corresponds to motion events experienced by the user 18 wearing the display device 14. The display device 14 may then utilize composite motion data from the smart phone to more accurately adjust the registration location of an image 26 to compensate for relative motion between the display device 14 and the user 18. Other examples of computing devices that may be utilized as companion devices as described above include, but are not limited to, navigation systems, entertainment systems, and other computing devices or sensors integrated into a vehicle, and wristwatches and other wearable computing devices.

Figure 10B:
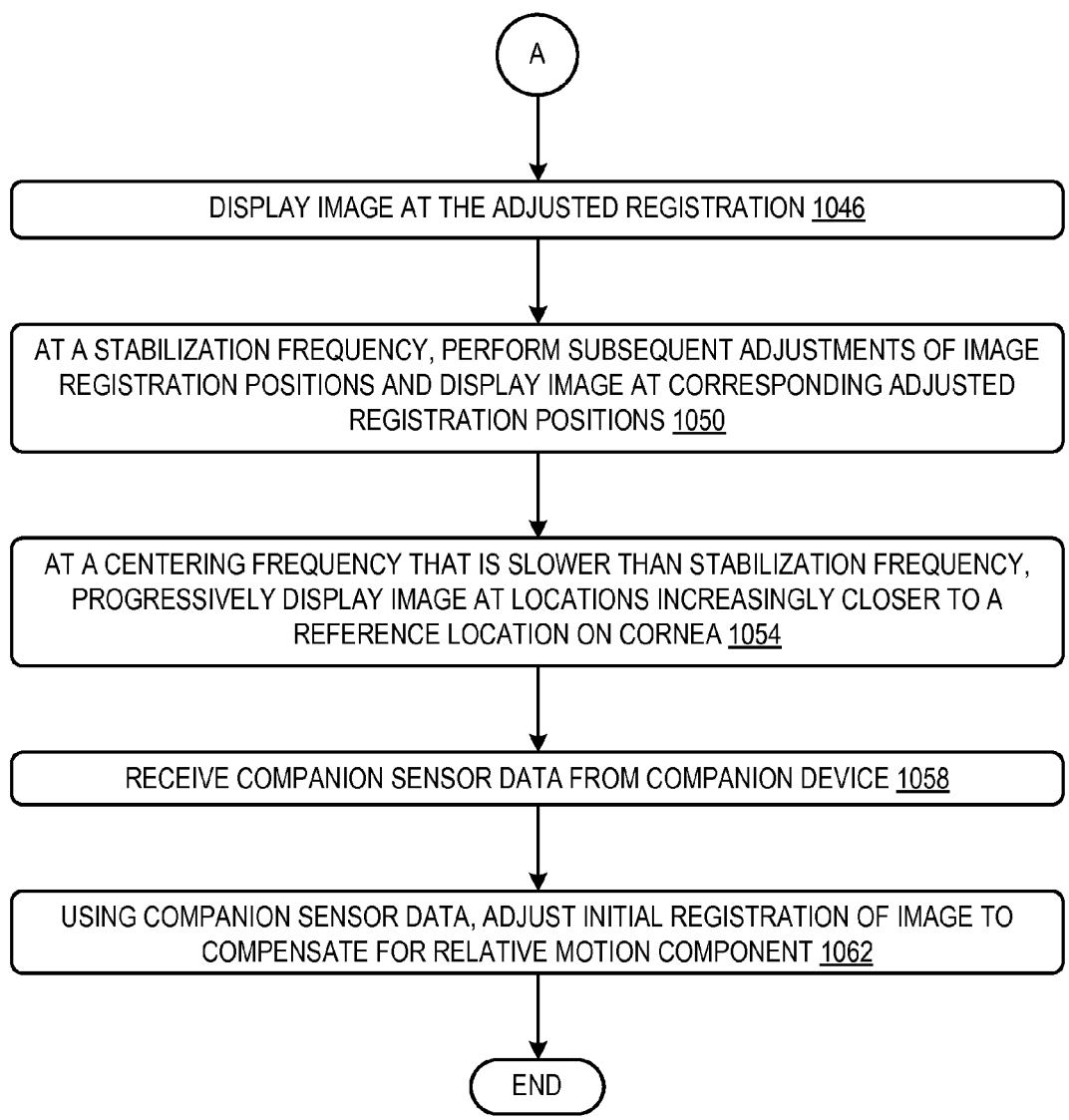

FIGS. 10A and 10B illustrate a flow chart of a method 1000 for displaying an image via a display device worn on a head of a user according to an embodiment of the present disclosure. The following description of method 1000 is provided with reference to the software and hardware components of the display device 14 described above and shown in FIGS. 1-9. It will be appreciated that method 1000 may also be performed in other contexts using other suitable hardware and software components.

With reference to FIG. 10A, at 1002 the method 1000 may include displaying the image at an initial registration position with respect to an eye of the user. At 1006 the method 1000 may include receiving composite motion data from one or more sensors of the display device, with the composite motion data comprising a head motion component and a relative motion component which is relative motion between the head and the display device. At 1010 the one or more sensors comprise two accelerometers. At 1014 the one or more sensors comprise an optical sensor.

At 1018 the method 1000 may include filtering the composite motion data to remove the head motion component and yield the relative motion component. At 1022 filtering the composite motion data may further comprise applying an adaptive filter or a high-pass filter to the composite motion data. At 1026 the method 1000 may include, using the relative motion component, adjusting the initial registration position of the image to an adjusted registration position with respect to the eye of the user that compensates for the relative motion component.

At 1030 the method 1000 may include using machine learning to adjust the initial registration position of the image. At 1034 the method 1000 may include adjusting the initial registration position of the image further by translating one or more pixels of the image. At 1038 the method 1000 may include adjusting the initial registration position of the image by moving one or more optical components of the display device. At 1042 the method 1000 may include adjusting the initial registration position of the image by moving a projector assembly of the display device.

With reference now to FIG. 10B, at 1046 the method 1000 may include displaying the image at the adjusted registration position. At 1050 the method 1000 may include, at a stabilization frequency performing subsequent adjustments of image registration positions and displaying the image at corresponding adjusted registration positions. At 1054 the method 1000 may include, at a centering frequency that is slower than the stabilization frequency, progressively displaying the image at locations increasingly closer to a reference location on the cornea. At 1058 the method 1000 may include receiving companion sensor data from a companion device. At 1062 the method 1000 may include, using the companion sensor data, adjusting the initial registration position of the image to compensate for the relative motion component.

It will be appreciated that method 1000 is provided by way of example and is not meant to be limiting. Therefore, it is to be understood that method 1000 may include additional and/or alternative steps than those illustrated in FIGS. 10A and 10B. Further, it is to be understood that method 1000 may be performed in any suitable order. Further still, it is to be understood that one or more steps may be omitted from method 1000 without departing from the scope of this disclosure.

Figure 11:
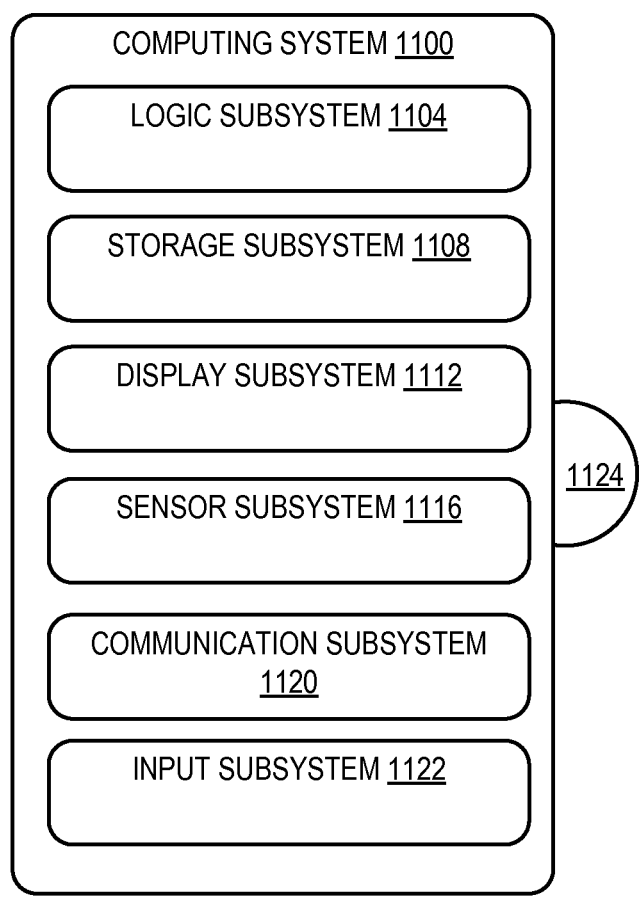
FIG. 11 is a simplified schematic illustration of an embodiment of a computing device.

FIG. 11 schematically shows a nonlimiting embodiment of a computing system 1100 that may perform one or more of the above described methods and processes. Computing device 30 and mobile computing device 86 may take the form of computing system 1100. Computing system 1100 is shown in simplified form, and may represent any suitable type of computing device or component. It is to be understood that virtually any computer architecture may be used without departing from the scope of this disclosure. In different embodiments, computing system 1100 may be integrated into display device 14, or may take the form of a mobile computing device such as a smart phone, laptop, notebook or tablet computer, desktop computing device, network computer, home entertainment computer, interactive television, gaming system, portable media player, gaming device, etc.

As shown in FIG. 11, computing system 1100 includes a logic subsystem 1104 and a storage subsystem 1108. Computing system 1100 may optionally include a display subsystem 1112, sensor subsystem 1116, communication subsystem 1120, input subsystem 1122 and/or other subsystems and components not shown in FIG. 11. Computing system 1100 may also include computer readable media, with the computer readable media including computer readable storage media and computer readable communication media. Further, in some embodiments the methods and processes described herein may be implemented as a computer application, computer service, computer API, computer library, and/or other computer program product in a computing system that includes one or more computers.

Logic subsystem 1104 may include one or more physical devices configured to execute one or more instructions. For example, the logic subsystem 1104 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem 1104 may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Storage subsystem 1108 may include one or more physical, persistent devices configured to hold data and/or instructions executable by the logic subsystem 1104 to implement the herein described methods and processes. When such methods and processes are implemented, the state of storage subsystem 1108 may be transformed (e.g., to hold different data).

Storage subsystem 1108 may include removable media and/or built-in devices. Storage subsystem 1108 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Storage subsystem 1108 may include devices with one or more of the following characteristics:

volatile, nonvolatile, dynamic, static, read/write, read-only, random access, sequential access, location addressable, file addressable, and content addressable.

In some embodiments, aspects of logic subsystem 1104 and storage subsystem 1108 may be integrated into one or more common devices through which the functionally described herein may be enacted, at least in part. Such hardware-logic components may include field-programmable gate arrays (FPGAs), program- and application-specific integrated circuits (PASIC/ASICs), program- and application-specific standard products (PSSP/ASSPs), system-on-a-chip (SOC) systems, and complex programmable logic devices (CPLDs), for example.

FIG. 11 also shows an aspect of the storage subsystem 1108 in the form of removable computer readable storage media 1124, which may be used to store data and/or instructions executable to implement the methods and processes described herein. Removable computer-readable storage media 1124 may take the form of CDs, DVDs, HD-DVDs, Blu-Ray Discs, EEPROMs, and/or floppy disks, among others.

It is to be appreciated that storage subsystem 1108 includes one or more physical, persistent devices. In contrast, in some embodiments aspects of the instructions described herein may be propagated in a transitory fashion by a pure signal (e.g., an electromagnetic signal, an optical signal, etc.) that is not held by a physical device for at least a finite duration. Furthermore, data and/or other forms of information pertaining to the present disclosure may be propagated by a pure signal via computer-readable communication media.

Display subsystem 1112 may be used to present a visual representation of data held by storage subsystem 1108. As the above described methods and processes change the data held by the storage subsystem 1108, and thus transform the state of the storage subsystem, the state of the display subsystem 1112 may likewise be transformed to visually represent changes in the underlying data. The display subsystem 1112 may include one or more display devices utilizing virtually any type of technology. Such display devices may be combined with logic subsystem 1104 and/or storage subsystem 1108 in a shared enclosure, such as in the eyeglasses 200, or such display devices may be peripheral display devices. The display subsystem 1112 may include, for example, the display system 22 of display device 14.

Sensor subsystem 416 may include one or more sensors configured to sense different physical phenomenon (e.g., acceleration, orientation, position, visible light, infrared light, sound, touch, pressure, etc.). Sensor subsystem 1116 may be configured to provide sensor data to logic subsystem 1104, for example. As described above, in some examples the sensor subsystem 1116 may comprise one or more accelerometers configured to sense acceleration and track motion. In other examples sensor subsystem 1116 may include image sensors configured to acquire images facing toward and/or away from a display device and/or any other suitable sensors that may be used to perform the methods and processes described above.

Communication subsystem 1120 may be configured to communicatively couple computing system 1100 with one or more networks and/or one or more other computing devices. Communication subsystem 1120 may include wired and/or wireless communication devices compatible with one or more different communication protocols. As nonlimiting examples, the communication subsystem 1120 may be configured for communication via a wireless telephone network, a wireless local area network, a wired local area network, a wireless wide area network, a wired wide area network, etc. In some embodiments, the communication subsystem may allow computing system 1100 to send and/or receive messages to and/or from other devices via a network such as the Internet.

Input subsystem 1122 may comprise or interface with one or more sensors or user-input devices such as a game controller, gesture input detection device, voice recognizer, inertial measurement unit, keyboard, mouse, or touch screen. In some embodiments, the input subsystem 1122 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

The term "program" may be used to describe an aspect of the present disclosure that is implemented to perform one or more particular functions. In some cases, such a program may be instantiated via logic subsystem 1104 executing instructions held by storage subsystem 1108. It is to be understood that different programs may be instantiated from the same application, service, code block, object, library, routine, API, function, etc. Likewise, the same program may be instantiated by different applications, services, code blocks, objects, routines, APIs, functions, etc. The term "program" is meant to encompass individual or groups of executable files, data files, libraries, drivers, scripts, database records, etc.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method for displaying an image via a display device worn on a head of a user, the display device including one or more sensors, the method comprising:
   displaying the image at an initial registration position with respect to an eye of the user;
   receiving composite motion data from the one or more sensors, the composite motion data comprising a head motion component and a relative motion component which is relative motion between the head and the display device;
   filtering the composite motion data to remove the head motion component and yield the relative motion component;
   using the relative motion component, adjusting the initial registration position of the image to an adjusted registration position with respect to the eye of the user that compensates for the relative motion component;

displaying the image at the adjusted registration position by projecting the image onto a cornea of the eye;

at a stabilization frequency, performing subsequent adjustments of image registration positions using relative motion components;

displaying the image at adjusted registration positions corresponding to the subsequent adjustments of the image registration positions;

at a centering frequency that is slower than the stabilization frequency, performing centering adjustments of image registration positions that progressively locate the image closer to a reference location on the cornea; and displaying the image at adjusted registration positions corresponding to the centering adjustments of the image registration positions.

2. The method of claim 1, wherein the one or more sensors comprise two accelerometers.

3. The method of claim 1, wherein the one or more sensors comprise an optical sensor.

4. The method of claim 1, wherein filtering the composite motion data further comprises applying an adaptive filter or a high-pass filter to the composite motion data.

5. The method of claim 1, further comprising using machine learning to adjust the initial registration position of the image.

6. The method of claim 1, wherein adjusting the initial registration position of the image further comprises translating one or more pixels of the image.

7. The method of claim 1, wherein adjusting the initial registration position of the image further comprises moving one or more optical components of the display device.

8. The method of claim 1, wherein adjusting the initial registration position of the image further comprises moving a projector assembly of the display device.

9. The method of claim 1, further comprising:
receiving companion sensor data from a companion device; and
using the companion sensor data, adjusting the initial registration position of the image to compensate for the relative motion component.

10. A display device configured to be worn on a head of a user and to display an image, the display device comprising:
a computing device;
one or more sensors communicatively coupled to the computing device;
a display system configured to display the image at an initial registration position with respect to an eye of the user; and
an image stabilization program stored in a mass storage of the computing device, the image stabilization program configured to:
receive composite motion data from the one or more sensors, the composite motion data comprising a head motion component and a relative motion component which is relative motion between the head and the display device;
filter the composite motion data to remove the head motion component and yield the relative motion component;
using the relative motion component, adjust the initial registration position of the image to an adjusted registration position with respect to the eye of the user that compensates for the relative motion component;

display the image at the adjusted registration position by projecting the image onto a cornea of the eye;

at a stabilization frequency, perform subsequent adjustments of image registration positions using relative motion components;

display the image at adjusted registration positions corresponding to the subsequent adjustments of the image registration positions;

at a centering frequency that is slower than the stabilization frequency, perform centering adjustments of image registration positions that progressively locate the image closer to a reference location on the cornea; and display the image at adjusted registration positions corresponding to the centering adjustments of the image registration positions.

11. The display device of claim 10, wherein the one or more sensors comprise two accelerometers.

12. The display device of claim 10, wherein the one or more sensors comprise an optical sensor.

13. The display device of claim 10, wherein the image stabilization program is further configured to filter the composite motion data by applying an adaptive filter or a high-pass filter to the composite motion data.

14. The display device of claim 10, wherein the image stabilization program is further configured to adjust the initial registration position of the image using machine learning.

15. The display device of claim 10, wherein the image stabilization program is further configured to adjust the initial registration position of the image by translating one or more pixels of the image.

16. The display device of claim 10, wherein the image stabilization program is further configured to adjust the initial registration position of the image by moving one or more optical components of the display device.

17. The display device of claim 10, wherein the image stabilization program is further configured to adjust the initial registration position of the image by moving a projector assembly of the display device.

18. A display device configured to be worn on a head of a user and operatively connected to a computing device, the display device configured to display an image on a cornea of an eye of the user, the display device comprising:
one or more sensors communicatively coupled to the computing device;
a display system configured to display the image at an initial registration position with respect to the cornea; and
an image stabilization program stored in a mass storage of the computing device, the image stabilization program configured to:
receive composite motion data from the one or more sensors, the composite motion data comprising a head motion component and a relative motion component which is relative motion between the head and the display device;
filter the composite motion data to remove the head motion component and yield the relative motion component;
using the relative motion component, adjust the initial registration position of the image to an adjusted registration position with respect to the cornea that compensates for the relative motion component;
display the image at the adjusted registration position;

at a stabilization frequency, perform subsequent adjustments of image registration positions using relative motion components;

display the image at adjusted registration positions corresponding to the subsequent adjustments of the image registration positions;

at a centering frequency that is slower than the stabilization frequency, perform centering adjustments of image registration positions that progressively locate the image closer to a reference location on the cornea; and display the image at adjusted registration positions corresponding to the centering adjustments of the image registration positions.

\* \* \* \* \*